United States Patent
Bergstoel

Patent Number: 6,126,606
**Date of Patent: *Oct. 3, 2000**

[54] ULTRASOUND PROBE MAINTAINING AN OPERABLE PRESSURE IN A PROBE FLUID CHAMBER

[75] Inventor: Svein Bergstoel, Sandefjord, Norway

[73] Assignee: GE Vingmed Ultrasound A/S, Horten, Norway

[ * ] Notice: This patent issued on a continued prosecution application filed under 37 CFR 1.53(d), and is subject to the twenty year patent term provisions of 35 U.S.C. 154(a)(2).

[21] Appl. No.: 09/137,620
[22] Filed: Aug. 21, 1998
[51] Int. Cl.$^7$ ........................................ A61B 8/14
[52] U.S. Cl. ............................................ 600/459
[58] Field of Search .................... 600/446, 459, 600/463, 466, 467, 464; 73/642, 472

[56] References Cited

U.S. PATENT DOCUMENTS

| | | |
|---|---|---|
| 4,784,148 | 11/1988 | Dow et al. ............................. 600/446 |
| 5,049,130 | 9/1991 | Powell .................................. 600/467 |
| 5,400,785 | 3/1995 | Crowley ................................ 600/467 |

OTHER PUBLICATIONS

Schematic Diagram Illustrating a Mechanical Probe Assembly in Cross–Section.
Brochure, "Family of Wideband Transesophageal Annular Array Transducers", Nov. 1998.

*Primary Examiner*—Marvin M. Lateef
*Assistant Examiner*—Ali M. Imam
*Attorney, Agent, or Firm*—McAndrews Held & Malloy; Christian G. Cabou; Phyllis Y. Price

[57] ABSTRACT

The present invention is directed to an apparatus for the prevention of foreign matter invasion into a fluid chamber of a probe. The apparatus comprises a tube coupled to a fluid chamber, wherein the tube has a first end and a second end. The first tube end is maintained in open fluid communication with the fluid chamber. The second tube end is maintained in open communication with atmospheric pressure. The tube is configured to maintain an operable pressure within the fluid chamber via capillary forces during variant pressure changes within the fluid chamber.

36 Claims, 4 Drawing Sheets

ULTRASOUND PROBE MAINTAINING AN OPERABLE PRESSURE IN A PROBE FLUID CHAMBER

FIELD OF THE INVENTION

The present invention relates to ultrasonic transducer probes. More specifically, the present invention relates to the prevention of foreign matter, such as gas, from entering the fluid chamber of an ultrasonic transducer probe.

BACKGROUND

Current endoscopic technology allows trained medical personnel to insert an ultrasonic transducer probe into the body for the purpose of obtaining internal images of the body through the use of ultrasound technology. These ultrasound images assist technicians in diagnosing various internal conditions without the need to perform invasive exploratory surgery.

Conventional ultrasonic transducer probes are comprised of a transducer array enclosed within an acoustic fluid chamber. Acoustic fluid contained within the chamber is provided to assist in the propagation of ultrasound pulses in the area between the transducer array and transducer array lens. Further, the transducer tip utilizes a combination of mechanical seals and gaskets in order to retain the acoustic fluid within the chamber.

Typically, a transmission assembly is provided within the probe for manipulating or moving the transducer array or transducer tip about the probe. The transducer tip is typically coupled to an elongated flexible probe tube which allows the transducer tip to be inserted into the body from a remote position outside of the body. The elongated flexible probe tube is itself attached to a control handle having a steering device to control the movement and direction of the elongated flexible probe tube.

In operation, the transducer array, which is contained within the chamber, generates a series of ultrasound pulses which are transmitted from the transducer array, through the acoustic fluid contained in the chamber, and out through the transducer array lens towards a target area. Accordingly, the pulses are reflected back from the target through the transducer array lens into the chamber and through the acoustic fluid to the transducer array.

In order to operate in accordance with the designed intent, however, the acoustic fluid contained within the chamber must be kept free from foreign matter, such as gas. Nevertheless, such foreign matter may enter the chamber through mechanical seals and gaskets, used to retain the fluid within the chamber, resulting in a contamination of the acoustic fluid. The foreign matter is able to enter the fluid chamber through the mechanical seals and gaskets primarily as a result of pressure and temperature variations which act directly or indirectly upon the acoustic fluid contained within the chamber. If the acoustic fluid actually becomes contaminated, the foreign matter interferes with the propagation of the ultrasound pulses through the acoustic fluid causing the ultrasound pulses to be randomly reflected and dispersed about the chamber. Such foreign matter interference leads to a marked degradation in the quality of the images which are generated from the ultrasound pulses.

For example, during normal operation and transportation, the acoustic fluid contained within the chamber is subject to fluctuations and variations in both temperature and pressure. As a result of the variations in temperature, the fluid within the chamber expands and contracts thereby creating a chance of foreign matter introduction into the fluid and the chamber.

For instance, in normal operation wherein the probe is inserted into the body, the temperature of the acoustic fluid within the chamber typically rises. The rise in temperature is mainly attributed to such heat sources as internal body heat and the heat generated by the transducer array as ultrasound pulses are generated. As the temperature of the acoustic fluid in the chamber starts to rise, the acoustic fluid starts to expand and assert pressure against the internal surfaces of the chamber. As pressure is asserted against the internal surfaces of the chamber, the internal pressure of the chamber rises forcing the acoustic fluid out of the chamber through the associated mechanical seals and gaskets. Correspondingly, when the acoustic fluid in the chamber cools from such a heated state, the acoustic fluid necessarily contracts creating a vacuum within the chamber. The vacuum within the chamber draws air or gas, or possibly body liquids, into the chamber through the mechanical seals and gaskets, thereby introducing foreign matter into the acoustic fluid of the chamber.

Similarly, when the probe is inserted into a body, the pressure within the chamber typically rises from pressure being asserted against the array lens. Such pressure is typically caused by the internals of the body exerting pressure against the array lens. As the pressure acting on the array lens rises, the acoustic fluid contained within the chamber correspondingly asserts a proportional pressure against the internal surfaces of the chamber. As pressure is asserted against the internal surfaces of the chamber, the internal pressure of the chamber rises forcing the acoustic fluid out of the chamber through the mechanical seals and gaskets. Accordingly, when the pressure acting on the array lens subsides, the internal pressure of the chamber subsides creating a vacuum within the chamber. The vacuum within the chamber draws air or gas, or possibly body liquids, into the chamber through the mechanical seals and gaskets, thereby introducing foreign matter into the acoustic fluid and chamber.

Likewise, similar temperature and pressure variations can occur when the transducer probe stored or is transported, thereby creating an opportunity for the introduction of foreign matter into the chamber of the probe. For example, in air transport there are temperature and pressure variations which create similar conditions as those illustrated above, wherein foreign matter may be introduced into the acoustic fluid of the chamber.

Currently available transducer probes address contamination problems by various solutions directed towards the removal of foreign matter from an acoustic liquid, the foreign matter typically being air bubbles. Such solutions range from the usage of acoustic fluid reservoirs to chamber venting valves in order to remedy the foreign matter contamination. However, current technology is not directed towards preventing the contamination problem. Accordingly, the presently available solutions do not address the problem of preventing the contamination, but rather only remedy the contamination after it has already occurred. Further, current technology in the area does not address the common problems of pressure and temperature variations which take place within acoustic fluid chambers, leading to foreign matter introduction.

It is therefore desirable to provide an apparatus which can prevent the invasion of foreign matter into an acoustic fluid chamber as a result of such pressure and temperature variation that take place within acoustic fluid chambers.

SUMMARY OF THE INVENTION

The present invention is directed to an apparatus for the prevention of foreign matter invasion into a fluid chamber of a probe. In one embodiment, the apparatus comprises a capillary tube having a first and a second end, wherein the first end is in open communication with the acoustic fluid chamber. The open communication allows a volume of fluid from the acoustic fluid chamber to expand or contract within the capillary tube. The acoustic fluid contained within the capillary tube is retained within the capillary tube by capillary forces.

BRIEF DESCRIPTION OF THE DRAWINGS

The present invention is illustrated by way of example in the following drawings in which like references indicate similar elements. The following drawings disclose various embodiments of the present invention for purposes of illustration only and are not intended to limit the scope of the invention.

DETAILED DESCRIPTION

The following detailed description sets forth numerous specific details to provide a thorough understanding of the invention. However, those of ordinary skill in the art will appreciate that the invention may be practiced without these specific details. In other instances, well-known methods, procedures, and components, have not been described in detail so as not to obscure the invention.

The present invention is directed to an apparatus which prevents the invasion of foreign matter into an acoustic fluid chamber as a result of such pressure and temperature variation that take place within acoustic fluid chambers.

Figure 1:
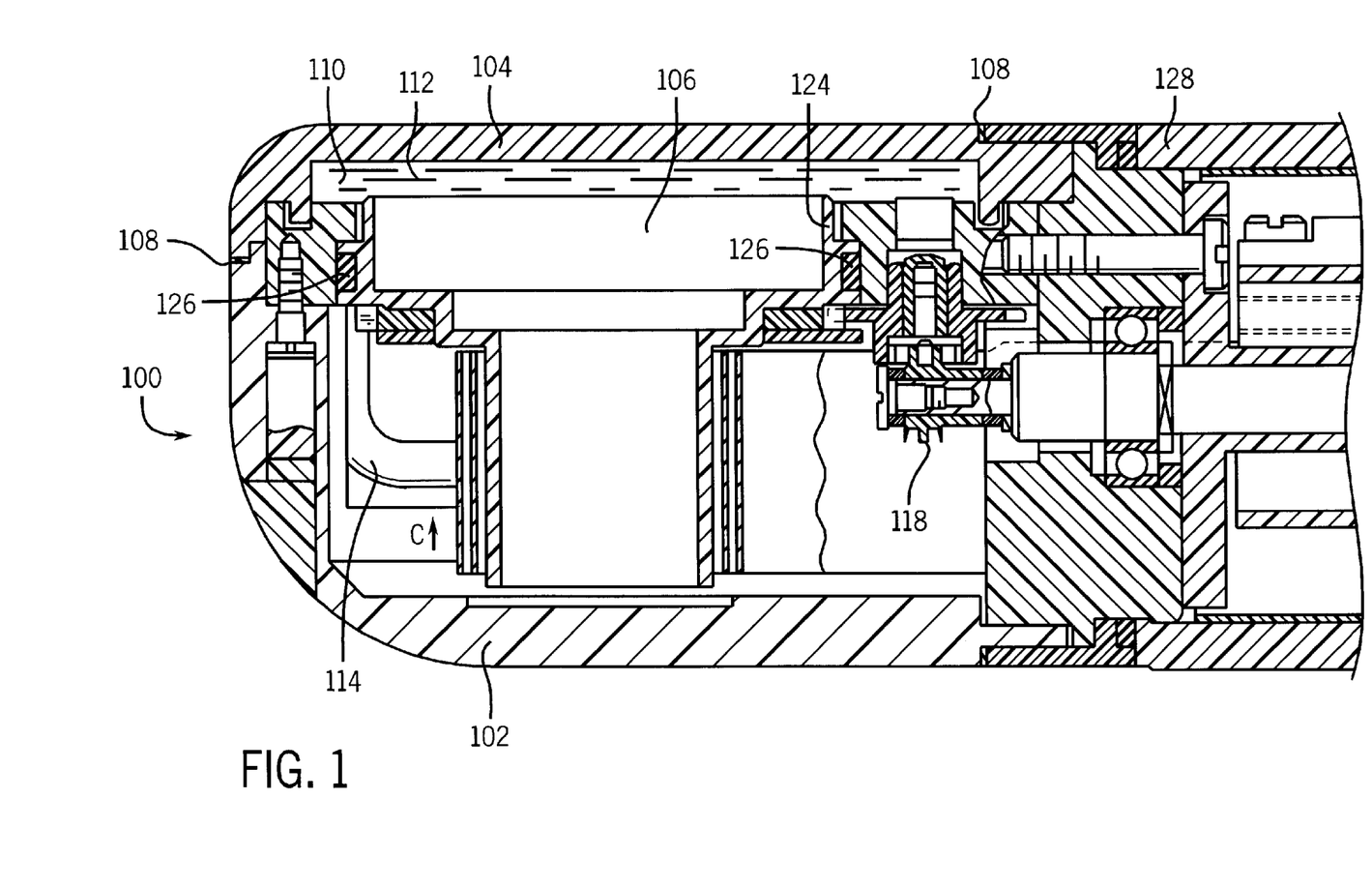
FIG. 1 is a cross-sectional view of a transducer tip assembly capable of implementing the teachings of the present invention.

FIG. 1 illustrates one embodiment of the present invention incorporated within an ultrasonic transducer tip 100 for use with an ultrasound probe. The ultrasonic transducer tip 100, illustrated in FIG. 1, includes a transducer tip casing 102 coupled to a transducer array lens (array lens) 104 with a transducer array 106 proximately disposed at an optimum location between the transducer tip casing 102 and the array lens 104. The array lens 104 may be coupled to the transducer tip casing 102 by a variety of methods, such as mutually threaded surfaces, heat bonded joints, or a variety of other fastening methods. In each of the aforementioned coupling methods, gaskets or sealing materials 108 are typically utilized between the respective contact mating surfaces of the array lens 104 and transducer tip casing 102. The array lens 104 is provided to allow for the unobstructed transmission and reception of ultrasound pulses by the transducer array 106. An acoustic fluid chamber area (acoustic chamber) 110 is disposed between the interior surface of the array lens 104 and the transducer array 106. The acoustic chamber 110 is formed by a section of the transducer tip or casing 102, the transducer array lens 104, and the transducer array 106. The acoustic chamber 110 is filled with an acoustic coupling fluid (acoustic fluid) 112. The acoustic fluid 112 being utilized to assist in the propagation of ultrasound pulses in the area between the transducer array 106 and the array lens 104.

Also shown in FIG. 1, a capillary type tube 114 is provided with the ultrasonic transducer tip 100. The capillary tube 114 is coupled to the acoustic chamber 110 via an orifice (not shown), through which the acoustic fluid 112 from the acoustic chamber 110 may expand and contract. The capillary tube 114 is in open fluid communication with acoustic fluid 112 contained in the acoustic chamber 110. The capillary tube 114 allows the acoustic fluid 112 in the acoustic chamber 110 to either expand or contract through the orifice and within the capillary tube 114, while maintaining a relatively stable internal pressure within the acoustic chamber 110. The capillary tube 114 may extend past the ultrasonic transducer tip 100 into the probe itself, or the capillary tube 114 may remain entirely within ultrasonic transducer tip 100, depending upon the desired length of the capillary tube 114 necessary for a particular application.

In one embodiment of the present invention, the capillary tube 114 is provided in an operable dimension for invasive operations. For example, the dimensions of the tube 114 are decreased (e.g., shortened and/or narrowed) relative to conventional capillary tubes used in ultrasound probes. As a result, less fluid 112 is placed in the fluid chamber 110 of the overall size of the chamber and probe is decreased. Therefore, the probe is more operable for invasive techniques.

Additionally, a transmission assembly 118 is shown coupled to the transducer array 106 through a series of gears and associated mechanical seals. The transmission assembly 118 allows for the movement of the transducer array 106 within the transducer tip 100. As illustrated, the transducer array 106 is retained within a movable cup shaped device 124 which incorporates mechanical seals 126 in order to retain the acoustic fluid 112 within the acoustic chamber 110. The transducer array 106 may be retained in any type of device which allows the desired manipulation of the transducer array 106. The transducer tip 100 is shown coupled to a portion of an elongated flexible probe tube 128, which enables the transducer tip 100 to be inserted through a small insertion point into the body. In one embodiment, the elongated flexible probe tube 128 is itself attached to a handle (not shown) having a steering device to control the movement and direction of the elongated flexible probe tube 128.

Figure 2:
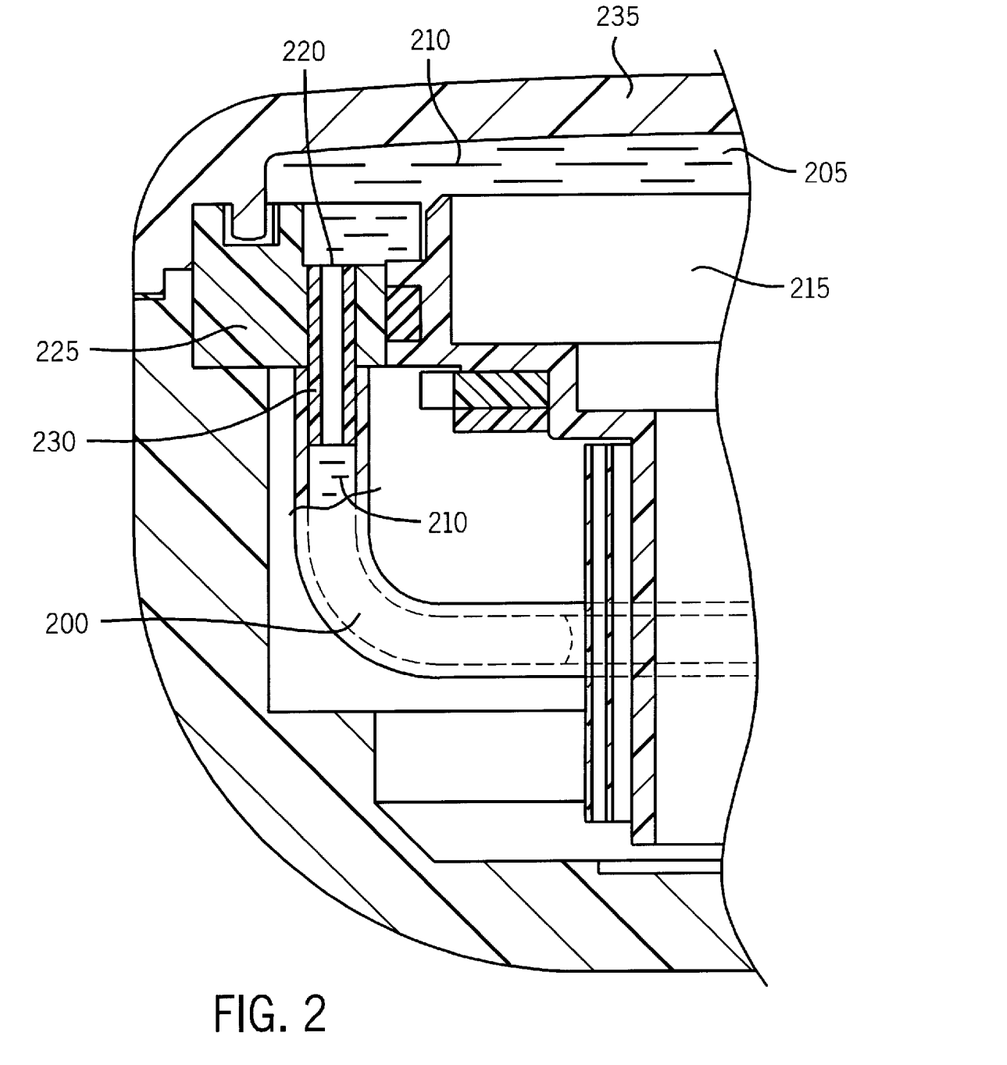
FIG. 2 is a partial cross-sectional view of a transducer tip assembly according to one embodiment of the present invention.

FIG. 2 illustrates, in further detail, a portion of the transducer tip of FIG. 1, showing the interconnection between the capillary tube 200 and the acoustic chamber 205. The capillary tube 200 typically contains a portion of acoustic fluid 210 within the capillary tube 200 in order to compensate for acoustic fluid 210 expansions and contractions which occur within the acoustic chamber 205. The actual capillary tube 200 connection point to the acoustic chamber 205 may be located at any point about the acoustic chamber 205 so as not to interfere with the transmission and reception of the ultrasound pulses associated with the transducer array 215.

The capillary tube 200, as shown in FIG. 2, is coupled with the acoustic chamber 205 through an orifice 220, allowing the acoustic fluid 210 from the acoustic chamber 205 to expand and contract through the orifice 220. Specifically, the capillary tube 200 is shown as coupled to a tube support member 225, the support member 225 having an area removed from the upper section of the support member 225 adjacent to the acoustic chamber 205. A support tube 230 is coupled to the bottom of the upper section of the support member 225, wherein the orifice 220 passes through the bottom of the upper section into the support tube 230. The capillary tube 200 is operatively coupled to the support tube 230, thereby allowing the acoustic fluid 210 in the acoustic chamber 205 to be in open fluid communication with the capillary tube 200. Accordingly, the orifice 220 allows a open fluid communication pathway for the acoustic fluid 210 from the acoustic chamber 205 to expand or contract within the capillary tube 200, thereby allowing the pressure within the acoustic chamber 205 to remain at a relatively constant value (operable pressure value) even with variations of pressure and temperature acting on the acoustic chamber 205. Likewise, the capillary tube 200, via capillary forces, maintains an operable pressure value within the acoustic chamber 205 without variations of pressure and temperature acting on the acoustic chamber 205.

The design of the capillary tube 200 may be based upon factors associated with both the acoustic fluid 210 and the array lens 235. For instance, the usage of a particular probe may be subject mostly to variations in temperature, wherein the design of the capillary tube 200 is primarily dictated by factors associated with the coefficient of volume expansion (E) of the acoustic fluid 210. The usage of another probe may be subject mostly to variations in pressure acting against the array lens 235, wherein the design of the capillary tube 200 may be dictated by factors associated with the maximum deflection of the array lens 235. Moreover, the usage of a particular probe may be subject to both variations in temperature and pressure, wherein the design of the capillary tube 200 could be dictated by factors associated with both the coefficient of volume expansion (E) and pressure acting against the array lens 235.

With respect to variations in temperature, the coefficient of volume expansion (E) of the acoustic fluid 210 is related to the acoustic fluid 210 used in the probe. The coefficient of volume expansion (E) associated with the acoustic fluid 210 is utilized in determining the proper operating length and diameter of the capillary tube 200. Since the coefficient of volume expansion (E) for the acoustic fluid 210 is known, the change of fluid volume ($\Delta V$) due to thermal expansion or contraction of the acoustic fluid 210 can be determined with reference to the changes in temperature ($\Delta T$).

In one embodiment, the change of fluid volume ($\Delta V$) can be determined by using the following physics formula for the coefficient of volume expansion (E) for a fluid $[E=(1/V) \times (\Delta V/\Delta T)]$, where V represents the initial volume of a liquid. For instance, if the coefficient of volume expansion (E) equals 0.2 cubic inches per degree, with the initial volume of fluid equaling 10 cubic inches, and the change in temperature is expected to be 2 Degrees, the change of fluid volume ($\Delta V$) would equal 4 cubic inches. Therefore, since the change in the volume of a fluid ($\Delta V$) due to thermal expansion and contraction can be calculated, the corresponding operating length of the capillary tube 200 necessary to accommodate acoustic may be easily calculated.

Accordingly, if the temperature of the acoustic fluid increases from T1 to T2 ($\Delta T$), an expansion in the volume ($\Delta V$) of the acoustic fluid 210 within the acoustic chamber 205 occurs. The expansion in the volume ($\Delta V$) of the acoustic fluid 210 within the acoustic chamber 205 causes a corresponding volume of acoustic fluid 210 to be forced out of the acoustic chamber 205 through the orifice 220 into the capillary tube 200. The volume of expanding fluid 210 displaces or pushes the portion of fluid 210 contained within the capillary tube 200 during expansion, from a first position to a second position along the interior of the capillary tube 200. Similarly, if the temperature of the acoustic fluid decreases from T1 to T2 ($\Delta T$), a corresponding volume of acoustic fluid 210 will be drawn into the acoustic chamber 205 from the capillary tube 200 during contraction, causing the fluid 210 within the capillary tube 200 to travel from a first position to a second position along the interior of the capillary tube 200. Therefore, the overall proper volumetric capacity and length of the capillary tube 200 can be mathematically determined with respect to the coefficient of volume expansion (E) and the expected change in volume ($\Delta V$) associated with the acoustic fluid 210.

With respect to variations in pressure, the maximum deflection (D) of the array lens 235 is typically a known value as the deflection of the array lens 235 is either supplied by the manufacturer or is determined by performing a simple lens deflection measurement. The maximum deflection (D) of the array lens 235 is utilized in determining the proper operating length and diameter of the capillary tube 200. Since the maximum deflection (D) of the array lens 235 is known, a volume displacement value (VD) of the acoustic fluid 210 can be determined based on the change in deflection ($\Delta D$) of the array lens 235. The volume displacement value (VD) corresponds to a volume of acoustic fluid 210 which will be displaced due to a change in deflection ($\Delta D$) of the array lens 235. Therefore, the volume displacement value (VD) of the fluid 210 may therefore be a function of the deflection ($\Delta D$) of the array lens 235. Alternately, a maximum volume displacement value (VDmax) could be determined by measuring the volume of fluid 210 displaced at the point of maximum deflection (D) of the array lens 235. Accordingly, the volume displacement value (VD) would be a function of the deflection ($\Delta D$) of the array lens 235 or VD=f($\Delta D$). Therefore, since the volume displacement value (VD) due to the deflection ($\Delta D$) of the array lens 235 can be calculated, the overall proper volumetric capacity and length of the capillary tube 200 can be mathematically determined with respect to the deflection ($\Delta D$) of the array lens 235 and the expected change in volume displacement (VD) of the acoustic fluid 235 which occurs as a result of the deflection of the array lens 235.

Therefore, if the deflection ($\Delta D$) of the array lens 235 increases from D1 to D2, a corresponding volume of acoustic fluid 210 will enter the capillary tube 210 from the acoustic chamber 205 during positive deflection (i.e.—the array lens 235 is pushed toward the transducer array 215), and travel from a first position (P1) to a second position (P2) along the interior of the capillary tube 200. Similarly, if the deflection ($\Delta D$) of the array lens decreases from D1 to D2, a corresponding volume of acoustic fluid 210 will enter into the acoustic chamber 205 from the capillary tube 205 during negative deflection (i.e.—the array lens 235 is released and moves away from the transducer array 215), and travel from a first position (P1) to a second position (P3) along the interior of the capillary tube 200. Accordingly, the overall proper volume capacity and length of the capillary tube 200 can be mathematically determined with respect to the volume displacement value (VD) due to the deflection ($\Delta D$) of the array lens 235.

Figure 3A:
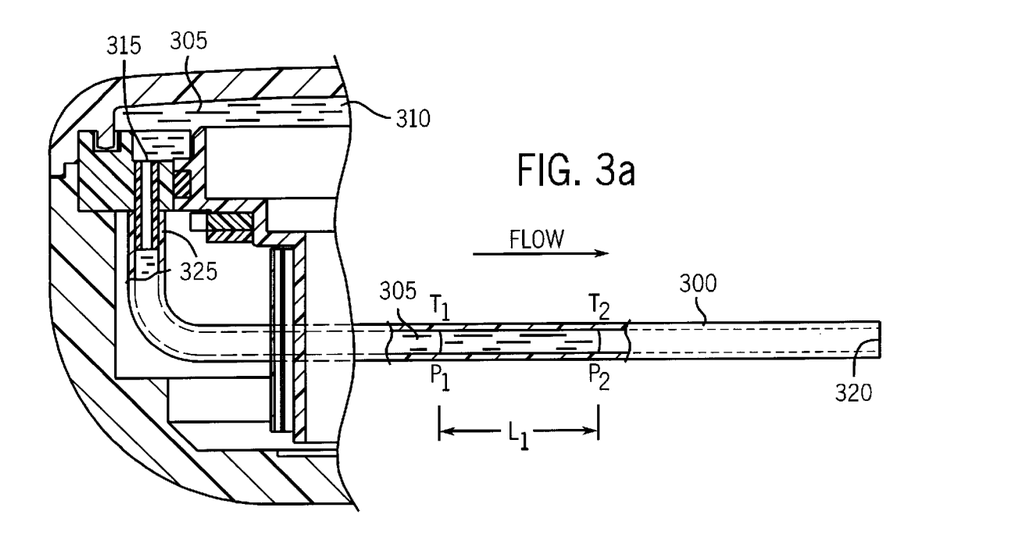
FIGS. 3a and 3b are cross-sectional views of one embodiment of a transducer tip assembly illustrating the operation of one embodiment of the present invention as relating to temperature variations.

FIG. 3a illustrates the operation of an open ended capillary tube 300 as the temperature of the acoustic fluid 305 in the acoustic chamber 310 increases. At an initial starting temperature (T1) the position of the acoustic fluid 305 within the capillary tube 300 corresponds to a initial position (P1). As the temperature of the acoustic fluid 305 within the acoustic chamber 310 rises to (T2), there is a corresponding increase in pressure which is exerted against the interior walls of the acoustic chamber 310. As the pressure within the acoustic chamber 310 rises, a specific volume of acoustic fluid 305 is forced out of the acoustic chamber 310 through the orifice 315 and into the capillary tube 300. Accordingly, the portion of acoustic fluid 305 contained within the capillary tube 300 is pushed toward the open end 320 of the capillary tube 300 from the initial position (P1) to a second position (P2), wherein the acoustic fluid 305 travels a specific length (L1) along the interior of the capillary tube 300. The capillary tube 300 is designed to allow a volume of acoustic fluid 305 to expand from the acoustic chamber 310 but remain within the capillary tube 300, while maintaining a constant and stable pressure within the interior of the acoustic chamber 310.

Figure 3B:
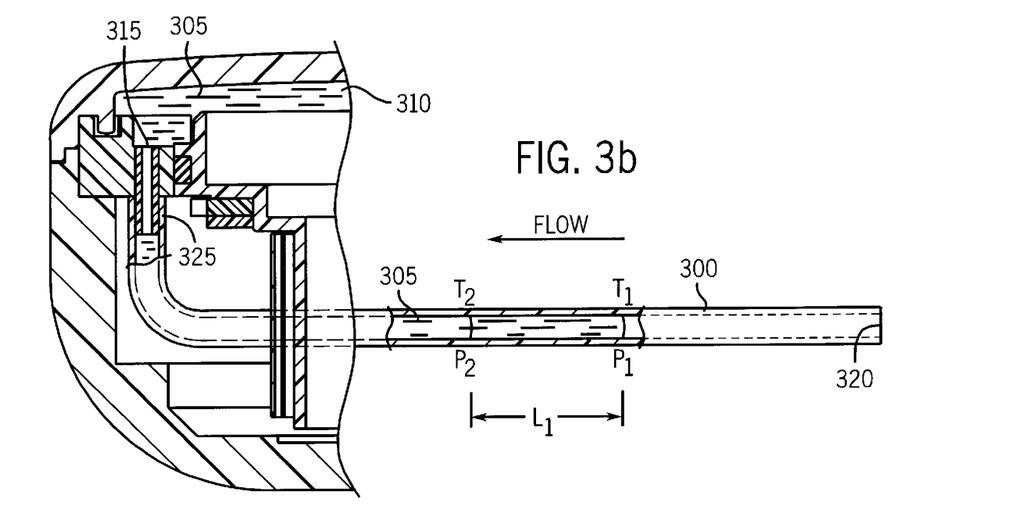

FIG. 3b illustrates the operation of the open ended capillary tube 300 as the temperature of the acoustic fluid 305 in the acoustic chamber 310 decreases. At an initial starting temperature (T1) the position of the acoustic fluid 305 within the capillary tube 300 corresponds to a initial position (P1). As the temperature of the acoustic fluid 305 within the acoustic chamber 310 decreases to (T2), there is a corresponding decrease in pressure which is exerted against the interior walls of the acoustic chamber 310 in the form of a vacuum. As the pressure within the acoustic chamber 310 decreases, a specific volume of acoustic fluid 305 is drawn into the acoustic chamber 310, through the orifice 315, from the capillary tube 300. Accordingly, that specific of volume of acoustic fluid 305 is drawn from the portion of acoustic fluid 305 contained within the capillary tube 300. Therefore, the portion of fluid 305 within the capillary tube is drawn toward the coupled end 325 of the capillary tube 300 adjacent the orifice 315 from the initial position (P1) to a second position (P2), wherein the acoustic fluid 305 travels a specific length (L1) along the interior of the capillary tube 300. The capillary tube 300 is designed to allow a volume of acoustic fluid 305 to contract within the acoustic chamber 310 with a portion of acoustic fluid 305 remaining within the capillary tube 300, while maintaining a constant and stable pressure within the interior of the acoustic chamber 310.

Figure 4A:
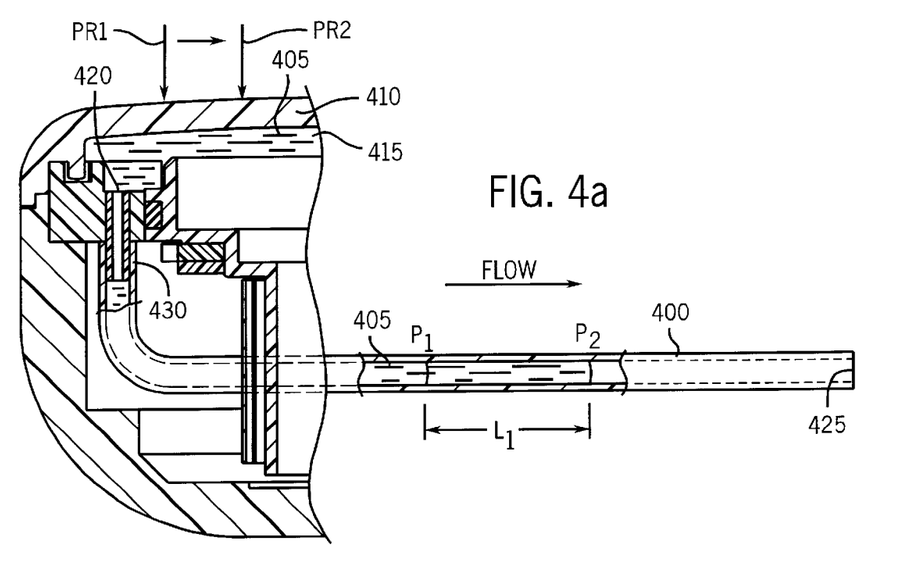
FIGS. 4a and 4b are cross-sectional views of one embodiment of a transducer tip assembly illustrating the operation of one embodiment of the present invention as relating to pressure variations.

FIG. 4a illustrates the operation of an open ended capillary tube 400 as the pressure acting on the acoustic fluid 405, through the array lens 410, increases, resulting in an increase in pressure within the acoustic chamber 415. At an initial neutral pressure (PR1) the position of the acoustic fluid 405 within the capillary tube 400 corresponds to a initial position (P1). As the pressure acting on the acoustic fluid 405 within the acoustic chamber 415 increases to (PR2), there is a corresponding increase in pressure which is exerted against the interior walls of the acoustic chamber 415. As the pressure within the acoustic chamber 415 increases, a specific volume of acoustic fluid 405 is forced out of the acoustic chamber 415 through the orifice 420 and into the capillary tube 400. Accordingly, the portion of acoustic fluid 405 within the capillary tube 400 is pushed toward the open end 425 of the capillary tube 400 from the initial position (P1) to a second position (P2), wherein the acoustic fluid 405 travels a specific length (L1) along the interior of the capillary tube 400. The capillary tube 400 is designed to allow a volume of acoustic fluid 405 to expand from the acoustic chamber 415 but remain within the capillary tube 400, while maintaining a constant and stable pressure within the interior of the acoustic chamber 415.

Figure 4B:
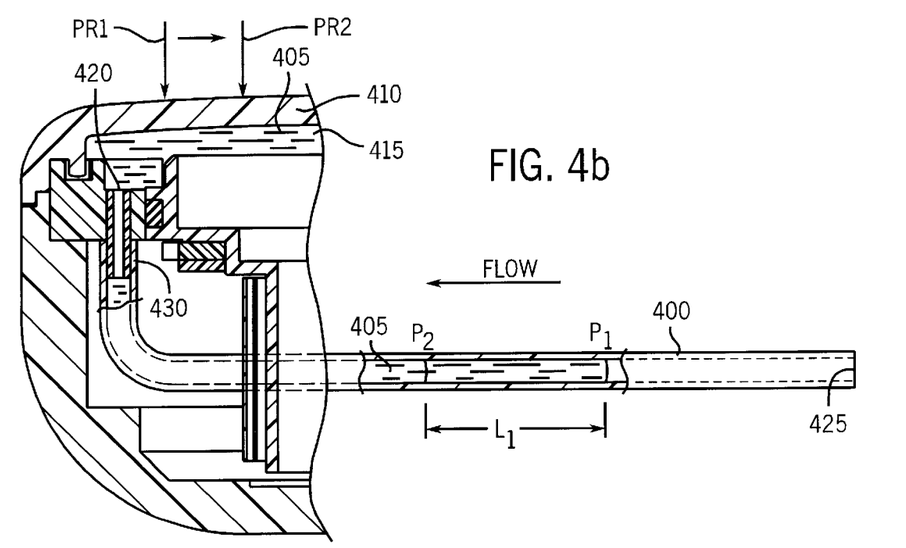

FIG. 4b illustrates the operation of the open ended capillary tube 400 as the pressure acting on the acoustic fluid 405, through the array lens 410, decreases, resulting in a decrease in pressure within the acoustic chamber 415. At an initial active pressure (PR1) the position of the acoustic fluid 405 within the capillary tube 400 corresponds to a initial position (P1). As the pressure acting on the acoustic fluid 405 within the acoustic chamber 415 decreases to (PR2), there is a corresponding decrease in pressure which is exerted against the interior walls of the acoustic chamber 415 in the form of a vacuum. As the pressure within the acoustic chamber 415 decreases, a specific volume of acoustic fluid 405 is drawn into the acoustic chamber 415 through the orifice 420 from the capillary tube 400. Accordingly, that specific of volume of acoustic fluid 405 is drawn from the portion of acoustic fluid 405 contained within the capillary tube 400. Therefore, the portion of acoustic fluid 405 within the capillary tube 400 is drawn toward the coupled end 430 of the capillary tube 400 adjacent to the orifice 420 from the initial position (P1) to a second position (P2), wherein the acoustic fluid 405 travels a specific length (L1) along the interior of the capillary tube 400. The capillary tube 400 is designed to allow a volume of acoustic fluid 405 to contract within the acoustic chamber 405 with a portion of the acoustic fluid 405 remaining within the capillary tube 400, while maintaining a constant and stable pressure within the interior of the acoustic chamber 415.

From the above description and drawings, it will be understood by those of ordinary skill in the art that the particular embodiments shown and described are for purposes of illustration only and are not intended to limit the scope of the invention. Those of ordinary skill in the art will recognize that the invention may be embodied in other specific forms without departing from its spirit or essential characteristics. References to details of particular embodiments are not intended to limit the scope of the claims.

What is claimed is:

1. An improved ultrasound probe comprising:
   a capillary tube having a first and a second end, the first end of the capillary tube in open communication with a fluid chamber and the second end of the capillary tube in open communication with atmospheric pressure, said capillary tube having an operable dimension for invasive operations, wherein the capillary tube has an associated tube length, the tube length corresponding with a lens deviation associated with a probe lens of the fluid chamber.

2. The probe of claim 1, wherein the capillary tube is configured to maintain an operable pressure within the fluid chamber via capillary forces throughout probe operation, transportation and storage.

3. The probe of claim 1, wherein the capillary tube is configured to allow a volume of fluid contained in the fluid chamber to expand or contract relative to the fluid chamber while maintaining an operable pressure within the fluid chamber throughout probe operation, transportation storage.

4. The probe of claim 3, wherein the capillary tube is configured to allow the volume of fluid contained in the fluid chamber to expand into the capillary tube when pressure in the fluid chamber increases.

5. The probe of claim 3, wherein the capillary tube is configured to allow a portion of fluid contained in the capillary tube to enter into the fluid chamber when pressure in the fluid chamber decreases.

6. The probe of claim 3, wherein the volume of fluid contained in the fluid chamber has an associated base temperature, the capillary tube being configured to allow the volume of fluid contained in the fluid chamber to expand into the capillary tube when the base temperature of the volume of fluid in the fluid chamber increases.

7. The probe of claim 3, wherein the volume of fluid contained in the fluid chamber has an associated base temperature, the capillary tube being configured to allow a portion of fluid contained in the capillary tube to enter into the fluid chamber when the base temperature of the volume in the fluid chamber decreases.

8. The probe of claim 1, wherein the capillary tube has an associated tube length, the tube length corresponding with a thermal expansion coefficient associated with the fluid.

9. The probe of claim 1, wherein said first end of said capillary tube is coupled to said fluid chamber through an orifice.

10. The probe of claim 1, further comprising:
a tube support member adjacent to said fluid chamber; and
a support tube coupled to a bottom of said tube support member and coupled to said first end of said capillary tube.

11. The probe of claim 1, wherein a length of said capillary tube is sufficient to allow fluid to expand from the fluid chamber but remain in the capillary tube.

12. The probe of claim 1, further comprising:
a transducer array located adjacent said fluid chamber, said tube having a first end coupled to said fluid chamber.

13. The probe of claim 1, further comprising:
a transducer casing;
a transducer array mounted in said transducer casing; and
an array lens coupled to said transducer casing and located proximate said transducer array, said transducer casing, transducer array and array lens defining the fluid chamber there between.

14. An improved ultrasound probe apparatus comprising:
a capillary tube coupled to a fluid chamber, the capillary tube having a first end and a second end, the first end in open fluid communication with the fluid chamber and the second end in open communication with atmospheric pressure, and said capillary tube configured to maintain an operable pressure within the fluid chamber via capillary forces during variant pressure changes within the fluid chamber, said capillary tube having an operable dimension for invasive operations, wherein the capillary tube has a tube length, the tube length corresponding to a lens deviation associated with a probe lens of the fluid chamber thereby maintaining an operable fluid range within the tube.

15. The apparatus of claim 14, wherein the capillary tube is configured to allow a volume of fluid contained in the fluid chamber to expand or contract relative to the fluid chamber while maintaining an operable pressure within the fluid chamber.

16. The apparatus of claim 15, wherein the capillary tube is configured to allow the volume of fluid contained in the fluid chamber to expand or contract in association with a portion of fluid retained within the first end of the capillary tube while maintaining an operable pressure within the fluid chamber.

17. The apparatus of claim 16, wherein the capillary tube is configured to allow the portion of fluid retained within the first end of the capillary tube to move toward the second end of the capillary tube when the volume of fluid contained in the fluid chamber expands.

18. The apparatus of claim 16, wherein the capillary tube is configured to allow the portion of fluid retained within the first end of the capillary tube to move toward the open fluid communication of the capillary tube when the volume of fluid contained in the fluid chamber expands.

19. The apparatus of claim 14, wherein the capillary tube has a tube length, the tube length corresponding to a thermal expansion coefficient associated with the fluid thereby maintaining an operable fluid range within the tube.

20. An ultrasound probe apparatus, the apparatus comprising:
a capillary tube coupled to a fluid chamber, the capillary tube having a first end and a second end, the first end in open fluid communication with the fluid chamber and the second end in open communication with atmospheric pressure; and
said first end is configured to retain a portion of fluid within the capillary tube via capillary forces, the portion of fluid being retained against a volume of fluid contained in the fluid chamber, said volume of fluid is retained within the fluid chamber via the capillary forces acting upon the portion of fluid contained within the capillary tube, said capillary tube having an operable dimension for invasive operations, wherein the capillary tube has an associated tube length, the tube length corresponding with a lens deviation associated with a probe lens of the fluid chamber.

21. The apparatus of claim 20, wherein the capillary tube is configured to maintain an operable pressure within the fluid chamber via capillary forces.

22. The apparatus of claim 20, wherein the capillary tube is configured to allow a volume of fluid contained in the fluid chamber to expand or contract relative to the fluid chamber while maintaining an operable pressure within the fluid chamber.

23. The apparatus of claim 20, wherein the capillary tube has an associated tube length, the tube length corresponding with a thermal expansion coefficient associated with the fluid.

24. The apparatus of claim 14, wherein said first end of said capillary tube is coupled to said fluid chamber through an orifice.

25. The apparatus of claim 14, further comprising:
a tube support member adjacent to said fluid chamber; and
a support tube coupled to a bottom of said tube support member and coupled to said first end of said capillary tube.

26. The apparatus of claim 14, wherein a length of said capillary tube is sufficient to allow fluid to expand from the fluid chamber but remain in the capillary tube.

27. The apparatus of claim 14, further comprising:
a transducer array located adjacent said fluid chamber, said tube having a first end coupled to said fluid chamber.

28. The apparatus of claim 14, further comprising:
a transducer casing;
a transducer array mounted in said transducer casing; and
an array lens coupled to said transducer casing and located proximate said transducer array, said transducer casing, transducer array and array lens defining the fluid chamber there between.

29. An ultrasound probe, comprising:
a transducer array;
a transducer casing housing said transducer array;
an array lens coupled to said transducer casing, said transducer array, transducer casing and array lens cooperating to define an acoustic fluid chamber there between;
an acoustic fluid filling said acoustic fluid chamber; and
a capillary tube located in said transducer casing and having a first end coupled to said acoustic fluid chamber, said acoustic fluid maintaining an operable fluid range in said capillary tube, said acoustic fluid expanding and contracting within said capillary tube while maintaining a relatively stable internal pressure in said acoustic fluid chamber.

30. The probe of claim 29, wherein said first end of said tube is coupled to said acoustic fluid chamber through a orifice.

31. The probe of claim 29, further comprising:

a tube support member adjacent said fluid chamber; and a support tube coupled to a bottom of said tube support member and to said first end of said tube.

32. An improved probe comprising:

a tube having a first and a second end, the first end of the tube in open communication with a fluid chamber and the second of the tube in open communication with atmospheric pressure, said tube having an operable dimension for evasive operations, said tube having an associated tube length, the tube length corresponding with a lens deviation associated with a probe lens of the fluid chamber.

33. An improved apparatus comprising:

a tube coupled to a fluid chamber, the tube having a first end and a second end, the first end in open fluid communication with the fluid chamber and the second end in open communication with atmospheric pressure, and said tube configured to maintain an operable pressure within the fluid chamber via capillary forces during variant pressure changes within the fluid chamber, wherein the tube has a tube length, the tube length corresponding to a lens deviation associated with a probe lens of the fluid chamber thereby maintaining an operable fluid range within the tube.

34. An apparatus, the apparatus comprising:

a capillary tube coupled to a fluid chamber, the capillary tube having a first end and a second end, the first end in open fluid communication with the fluid chamber and the second end in open communication with atmospheric pressure; and said first end is configured to retain a portion of fluid within the tube via capillary forces, the portion of fluid being retained against a volume of fluid contained in the fluid chamber, said volume of fluid is retained within the fluid chamber via the capillary forces acting upon the portion of fluid contained within the tube, the tube having an associated tube length, the tube length corresponding with a lens deviation associated with a probe lens of the fluid chamber.

35. An improved ultrasound probe comprising:

a transducer casing;

a transducer array mounted in said transducer casing;

an array lens coupled to said transducer casing and located proximate said transducer array, said transducer casing, transducer array and array lens defining a fluid chamber therebetween; and a capillary tube having a first and a second end, the first end of the capillary tube in open communication with the fluid chamber and the second end of the capillary tube in open communication with atmospheric pressure, said capillary tube having an operable dimension for invasive operations.

36. An improved ultrasound probe apparatus comprising:

a transducer casing;

a transducer array mounted in said transducer casing;

an array lens coupled to said transducer casing and located proximate said transducer array, said transducer casing, transducer array and array lens defining a fluid chamber therebetween; and a capillary tube coupled to the fluid chamber, the capillary tube having a first end and a second end, the first end in open fluid communication with the fluid chamber and the second in open communication with atmospheric pressure, said capillary tube being configured to maintain an operable pressure within the fluid chamber via capillary forces during variant pressure changes within the fluid chamber, said capillary tube having an operable dimension for evasive operations.

\* \* \* \* \*